United States Patent [19]

Stillman

[11] Patent Number: 4,664,914

[45] Date of Patent: May 12, 1987

[54] JOJOBA OIL COMPOSITIONS AND METHODS

[76] Inventor: Theodore Stillman, 517 E. Vista Chino, Palm Springs, Calif. 92262

[21] Appl. No.: 661,773

[22] Filed: Oct. 17, 1984

[51] Int. Cl.$^4$ ................... A61K 35/78; A61K 31/22; A61K 47/00

[52] U.S. Cl. ................ 424/195.1; 514/552; 514/784; 514/844; 514/944

[58] Field of Search ............ 424/195.1; 514/552, 514/784, 844, 944

[56] References Cited

U.S. PATENT DOCUMENTS

| | | | |
|---|---|---|---|
| 2,582,395 | 1/1952 | Rigby | 514/458 |
| 2,628,930 | 2/1953 | Zentner | 514/458 |
| 3,244,595 | 4/1966 | Feigh | 514/168 |
| 4,410,517 | 10/1983 | Stillman | 424/195.1 |

*Primary Examiner*—Johnnie R. Brown
*Assistant Examiner*—John W. Rollins, Jr.
*Attorney, Agent, or Firm*—Milton M. Field

[57] ABSTRACT

A dermatological coating material is prepared by combining 16 to 70 parts by weight of a glyceryl monostearate componet with 84 to 30 parts by weight of a Jojoba oil component to form a solution with the aid of heat, which solution, when cooled forms a frozen solid or semi-solid solution at room temperature. The frozen solution may be mixed, or aged at a slightly elevated temperature, to reduce crystal formation.

Utility as cosmetic bases, Vaseline substitutes, protective coatings, dermatological putties, hair groomers, lubricants, such as sexual lubricants, and stick cosmetics, such as lipsticks is shown.

The disclosed method is a technique for hardening Jojoba oil.

14 Claims, No Drawings

JOJOBA OIL COMPOSITIONS AND METHODS

This application is related to my prior applications Ser. No. 290,157, filed Aug. 5, 1981, now U.S. Pat. No. 4,410,517, issued Oct. 18, 1983 and Ser. No. 542,645, filed Oct. 17, 1983, now U.S. Pat. No. 4,551,332.

BACKGROUND OF THE INVENTION

1. Field of the Invention

This invention relates to frozen solutions of glyceryl monostearate with jojoba oil and the use of such solutions as substitutes for Vaseline, cosmetic bases, protective skin coatings, dermatological putties, lubricants such as sexual lubricants, hair groomers, stick cosmetics, hand lotions and as carriers for germicidal or therapeutic agents and to methods of making such compositions.

2. Brief Description of the Prior Art

Pure jojoba oil has been used directly on the skin. Because of the very low viscosity of the Jojoba oil, such uses have been far from satisfactory. It is an object of the invention to develop a technique for hardening or increasing the viscosity of jojoba oil.

As an outgrowth of my work leading to the development of vitamin E compositions as described in my U.S. Pat. No. 4,410,517 and my application Ser. No. 542,645, some of which include a jojoba oil component, I have explored the properties of compositions comprising frozen solutions of glyceryl monostearate and Jojoba oil. As explained more fully below, many of these compositions are improvements over prior art compositions. For example, although Vaseline has been widely used as a sexual lubricant, it has the undesirable property of not being easily biodegraded. It has been found that Vitamin E compositions applied to the skin, such as those disclosed in the aforementioned U.S. Pat. No. 4,410,517 and Ser. No. 542,645 aplication, cannot be used by people who have allergic reactions to Vitamin E. These problems are avoided by the compositions of the present invention.

SUMMARY OF THE INVENTION

A dermatological coating material (a term used herein generically to describe a number of preparations applied to the skin or hair) is prepared by combining glyceryl monostearate with jojoba oil to form a solution with the aid of heat, which solution, when cooled, forms a frozen solid or semi-solid solution at room temperature. In this solution, the glyceryl monostearate and jojoba oil are mutually soluable and, when in proper proportions, do not separate in storage. The frozen solution may be mixed or aged to eliminate or reduce crystal formation.

Embodiments are described which are used as a cosmetic base, as a substitute for solid petrolatum, as a protective coating, as a dermatological putty, as a carrier for germicidal or therapeutic agents, as a hair groomer, as a lubricant such as a sexual lubricant, as a stick cosmetic such as a lipstick, and a hand lotion.

The compositions are hypoallergenic, non-irritating and innocuous. The glyceryl monostearate component is biodegradable. Thus, the aforementioned problems of Vaseline and vitamin E compositions are avoided.

The method according to the invention is a useful technique for hardening jojoba oil.

DETAILED DESCRIPTION

In the following detailed description, the abbreviation GMS is used for glyceryl monostearate.

In general, the frozen solutions of the present invention will be manufactured by a method including the steps of:

(1) Putting all the ingredients into the same container and heating, preferably with steam, until the GMS melts and then mixing until a completely homogeneous solution is attained.

(2) The solution is permitted to cool to room temperature to form a frozen solution.

(3) In some cases it is necessary to mix a solution after it freezes to remove crystals. When this is called for, ordinary mixing will not suffice; such mixing requires pressure on the crystals. The only way to supply such pressure is to put the solution through a ball mill. The solution will be in a pipe with the solution having enough pressure on it to push a slightly fluid and still slightly warm partly frozen solution through a ball mill at just the right time after the homogeneous solution is formed. The right time is just after the molten solution freezes enough to form crystals but just before the molten solution becomes too frozen to be pumped through a pipe. This cooling requires some type of a cooling tower to remove the heat from piped solutions that come from a tank under pressure. Thus, large scale production that requires mixing after the molten solutions freeze are not simple to handle and mixing after a solution freezes is to be avoided if possible. It is, therefore, much simpler to pour the still molten homogeneous solution directly into their final containers. Alternatively, another technique for removing the crystals that form in the solutions involves aging the solutions, or aging them at a slightly elevated temperature, approximately 95° F. Such aging could take as little as a few days. In this time, the crystals will disappear themselves.

In a variation of the above method, the GSM is melted in a separate container and subsequently combined with the other ingredients (jojoba oil or primarily Jojoba oil) with the aid of sufficient heat to keep the GSM molten until a homogeneous solution is obtained.

Solutions of GMS and jojoba oil have lower viscosity than equivalent solutions of GMS and alpha-tocopherol acetate, as disclosed in my Ser. No. 542,645 application. However, the viscosity of GMS and jojoba oil solutions can be increased by increasing the concentration of GMS. Although these solutions are opaque and do not exactly duplicate the appearance of Vaseline, they can function as an adequate substitute for Vaseline in all of Vaseline's areas of use. Pure GMS and jojoba oil solutions have several major advantages. GMS and jojoba solutions are completely resistant to oxidation and completely free of toxic compounds. In addition, they are excellent sexual lubricants and excellent dermatological coatings. Due to the tendency of these solutions to crystalize, they tend to be less homogeneous. As explained above, this crystalization can be removed by a mixing or aging step. Removal of crystals by mixing also lowers viscosity significantly.

Dissolving appropriate concentrations of GMS into jojoba oil increases the viscosity of jojoba oil, transforming it into a solid or semisolid. This greatly enhances the utility of jojoba oil as a dermatological coating.

Table A, which follows, demonstrates the properties of various formulations with varying proportions of GMS and jojoba oil. In the table, the left-hand column identifies the formulation by number. The next column headed "GMS" provides the parts by weight of GMS. The column headed "Jojoba" gives the parts by weight of jojoba oil. The "Freezing Point" column provides the freezing point in degrees Fahrenheit. The remaining columns contain numbers which represent ratios between the characteristics of a sample and the characteristics of Vaseline. In all cases, unless otherwise stated, the sample was mixed or aged to reduce crystallization. Considering the tack of a sample, for example, assume that Vaseline has a tack of 1.0 and the sample has a tack of 1.5, the resulting tack factor would be 1.5 divided by 1. A factor of 1.0 means that the sample and Vaseline have the same properties as to the characteristic in question.

It is also to be noted from the table that tack increases as the GMS concentration increases. The tack is great enough for the solutions to function as dermatological putties in thin layers for compositions having GMS concentrations of 60 to 70 percent by weight and 40 to 30 percent by weight of jojoba oil.

It is thus clear that useful compositions include those with GMS concentrations greater than 15 parts by weight and less than 80 parts by weight and with jojoba oil concentrations less than 85 parts by weight and greater than 20 parts by weight. This establishes the useful ranges as 16 to 70 percent by weight of GMS and 84 to 30 percent by weight of jojoba oil.

In my copending application Ser. No. 542,645, I have described protective coating compositions incorporating clove oil as a germicidal agent. Similar compositions can be used with the compositions described in the preceding paragraph. As in the examples described in

TABLE A

| Example | GMS | Jojoba | Hardness | Reflect-ability | Lubri-cation | Trans-parency | Tack | Freeze Point °F. | Remarks |
| --- | --- | --- | --- | --- | --- | --- | --- | --- | --- |
| 1 | 10 | 90 | | | | | | 113 | Oil separates |
| 2 | 15 | 85 | | | | | | 115 | Bleeds oil on storage |
| 3 | 16 | 84 | 0.6 | 0.8 | 0.9 | 0.6 | 1.0 | 115 | Stable |
| 4 | 18 | 82 | 0.7 | 0.8 | 0.9 | 0.7 | 1.0 | 115 | Stable |
| 5 | 20 | 80 | 0.8 | 0.8 | 0.9 | 0.6 | 1.0 | 116 | Stable |
| 6 | 30 | 70 | 1.5 | 0.4 | 0.8 | 0.4 | 1.2 | 118 | Stable |
| 7 | 40 | 60 | 2.0 | 0.2 | 0.7 | 0.3 | 1.2 | 120 | Stable |
| 8 | 50 | 50 | 3.0 | 0.1 | 0.3 | 0.2 | 1.5 | 123 | Note 1 |
| 9 | 60 | 40 | 3.5 | 0.1 | 0.2 | 0.1 | 2.5 | 125 | Note 2 |
| 10 | 70 | 30 | 4.5 | 0.1 | 0.1 | 0.1 | 3.0 | 126 | Stable |
| 11 | 80 | 20 | 6.0 | 0.1 | 0 | 0 | 0 | 129 | Note 3 |

Note 1: Stable, but unmixed solutions are almost too hard to be scooped out.
Note 2: Stable, but unmixed solutions are too hard to be scooped out. Solution becomes a malleable tacky putty when mixed. However, it is not tacky enough to be applied in thick layers. Thin layers stick and form a tacky coating. Vitamin E solutions, as discussed in my application Serial No. 542,645, are much more tacky.
Note 3: Not malleable. Crumbles under pressure. Too hard to be scooped. Homogeneous without oil separation.

From Table A, it is concluded that GMS concentrations of 15 percent and lower do not adequately hold jojoba oil in solution. The transparencies of the solutions drop sharply for concentrations of GMS exceeding 20 percent. Thus, if one wishes to duplicate properties of Vaseline, one is limited to solutions which have GMS concentrations not exceeding 20 percent. Even at that concentration, it is apparent from the table that the transparency of the solution is only 60 percent of that of Vaseline.

It is also apparent from the table that the following formulations have good lubrication properties making them suitable for use as a lubricant, such as a sexual lubricant: compositions with 16 to 40 percent by weight of GMS and 84 to 60 percent by weight of jojoba oil. These solutions can be spread on the skin and provide adequate lubrication and relatively low tack. Transparency and reflectance do not affect the ability of the formulations to function as a lubricant. Due to the properties of GMS and jojoba oil, the solutions are inert in use; the solutions are not oxidizable, and are stable, hypoallergenic, non-irritating and safe to use.

The table also indicates that GMS and Jojoba oil compositions have properties suitable for functioning as foundations for stick cosmetics over the following ranges: 40 to 70 percent by weight GMS and 60 to 30 percent by weight of jojoba oil. Concentrations of 80 percent by weight of GMS and above result in compositions which crumble, making them unsuitable as stick cosmetic foundations.

the Ser. No. 542,645 application, the addition of from 1.5 to 4 parts by weight of clove oil to 100 parts by weight of the basic GMS and jojoba oil solution will result in a satisfactory protective coating for wounds.

It appears that in the GMS-jojoba oil solutions the GMS is the solvent and the jojoba oil is the solute. This is suggested by the effect of adding GMS to GMS-jojoba oil solutions from which jojoba oil separates (those with less than 16 percent by weight of GMS); the added GMS prevents such separation. It is thus an important discovery of this invention that GMS is a solvent for jojoba oil, a wax. The resulting solid solutions are solids because GMS is a solid at rooom temperature. The jojoba oil dissolves into the GMS when the GMS is in the molten state. That the molten GMS and jojoba oil form a solution is demonstrated by the fact that the molten solution which contains both GMS and jojoba oil forms a crystal clear homogeneous single phase solution. That a solid solution forms when the molten solution cools is proven by the fact that the oil does not separate provided that the concentration of GMS is high enough and by the fact that the resulting frozen solutions are homogeneous in the absence of crystals. While it is true that many of the GMS-jojoba oil solutions are not homogeneous in the frozen state, this is due to the formation of crystals which can be broken down by mixing. That there are crystals initially is proven by the higher melting point of the crystallized initially frozen GMS and Jojoba oil solutions as compared with the melting point of the noncrystallized mixed solutions.

If the crystallization was due to the separation of GMS and jojoba oil, the melting point of solutions which are primarily jojoba oil would not be higher, because free jojoba oil has a very low freezing point. Thus, solutions of 30 parts by weight of GMS and 70 parts by weight of jojoba oil could not contain completely free jojoba oil without showing oil separation and a decrease in the freezing point. There is, instead, an increase in the freezing point as the proportion of GMS oil increases, even though an increase in GMS creates an increase in crystallization. This indicates that intermolecular forces have increased with the formation of crystals. This indicates that both GMS and jojoba oil are similar enough to be part of some sort of crystallized structure.

I have thus far described a group of compositions that represent the foundations for a new cosmetic base or a new base for suspending therapeutic reagents. A new cosmetic base is defined as a group of compounds that can be put together in a variety of ways in order to make a variety of different cosmetics. This application describes the many ways of putting a new group of ingredients together and the many considerations that have to be considered in putting these ingredients together in order to produce the full range of cosmetics, from lipsticks to a hand lotion. Many of these considerations have been discussed above.

There are additional basic requirements for a cosmetic base: (1) the cosmetics that are produced from the group of ingredients that define the cosmetic base must not separate in storage and under a variety of climatic conditions; (2) the ingredients must not turn rancid or deteriorate into toxic or odorous compounds; (3) the ingredients must be put together in a way that will make them stable over a long period of time; (4) the compositions that are produced can be sterilized; (5) bacteria will not grow in the resulting compositions; (6) the ingredients of the group of compounds that represent the cosmetic base must be non-toxic and biodegradeable and a normal part of living biochemical pathways.

The resulting base can also be used to suspend a variety of therapeutic agents that could be considered dermatological medications. The resulting product would therefore be considered a dermatological medication. For example, antibiotics could be suspended in the above described cosmetic bases. This raises another requirement. The resulting bases must be viscous enough to prevent separation of solid or liquid ingredients that are added to said bases. All of the compositions that are disclosed herein are viscous enough to suspend solid or liquid additives. I shall now describe some beneficial products that can be produced by adding a variety of ingredients to the above described cosmetic or therapeutic bases.

A good stick cosmetic has to be soft enough to leave a small amount of cosmetic on the skin when it is rubbed on the skin. However, it should not be so soft that globs or large pieces are left on the skin; hardness is of great importance to a stick cosmetic. In addition, a good stick cosmetic should seem to be slippery. Thus, they are also good lubricants. The lubrication ability makes it easier to rub off the cosmetic on the skin without applying too much pressure; a cosmetic stick that requires a large amount of pressure is not a good cosmetic stick. Thus, the pressure required while applying a stick is an important criterion for evaluating cosmetic sticks. The amount that rubs off is also a vital criterion for evaluating stick cosmetics, especially if too much is put on the skin. The factor that is most likely to cause excess material to come off is a tendency for the stick to crumble or fall apart under the pressure needed to apply the cosmetic.

Table B, below, describes characteristics of cosmetic sticks made from GMS and jojoba oil. The criteria used to describe the experimental sticks are the criteria described above. These criteria are: (1) hardness, (2) tack, (3) lubrication, (4) pressure, and (5) amount removed by a single stroke of the finger.

The above criteria were measured by comparing the experimental sample with the three best cosmetic sticks already on the market. The experimental stick that is equivalent to the average of the cosmetic sticks that are currently being sold was given a reading of 1. Those samples with properties higher or lower than the average of the above three cosmetic sticks were given a reading that is higher or lower than 1. Thus, a sample that was given a reading of 1.5 under the vertical column entitled "hardness" will be 1.5 times as hard as the average of the hardness of the above three commercially sold cosmetic sticks. All readings are the average of the personal opinions of three separate observers. Thus, for example, three separate observers compared the tack of each separate experimental sample with the tack of the above three samples and determined the relative tack of the experimental sample. The same procedure was followed for hardness, lubrication, amount removed, and pressure required for applying sample to the skin.

While such a method of measurement may seem nonobjective, it should be kept in mind that the suitability of a cosmetic is a purely subjective matter. Only a user of a cosmetic can determine just how hard she must press in order to apply the stick cosmetic and the amount deposited will depend on how hard the user applies the stick. In addition, the ease with which the user applies the cosmetic will depend on how hard she presses the stick. Thus, the whole subject is subjective and measurements are best made by compiling an average of subjective opinions. Such averages are more likely to be closer to the opinions of the average public user.

In Table B, the "pressure" column describes the amount of pressure required to apply the cosmetic. The "amount rubbed off" column describes the amount of cosmetic removed in each application. The other columns are self-explanatory.

TABLE B

| Formulation | Stick Cosmetics | | | | | |
|---|---|---|---|---|---|---|
| | G.M.S. | Jojoba | Hardness | Tack | Lubrication | Pressure | Amount Rubbed Off |
| 12 | 30 | 70 | 0.7 | 1.0 | 1.0 | 1.0 | 2.0 |
| 13 | 40 | 60 | 0.9 | 1.0 | 1.0 | 1.0 | 1.0 |
| 14 | 50 | 50 | 1.1 | 1.0 | 1.0 | 1.3 | 1.0 |
| 15 | 60 | 40 | 1.3 | 0.8 | 0.7 | 1.5 | 0.8 |
| 16 | 70 | 30 | 1.5 | 0.7 | 0.6 | 1.7 | 0.5 |

From the above table, it is seen that formulations 13 through 16, covering a range of 40 to 70 parts by weight GMS and 60 to 30 parts by weight of jojoba oil, are suitable bases for stick cosmetics.

It is known that the viscosity of Vaseline is such that finely ground particles (minus 200 mesh) can be suspended in the Vaseline without fear that the particles will separate out. I will now consider the benefits of suspending or dissolving a variety of solids or liquids into the cosmetic bases of this invention, and I shall first discuss the difference between dissolving and suspending ingredients in the above bases.

A variety of dyes have been approved for use in drugs and cosmetics, such as D and C red #6 BA LAKE, D and C red #7 AL LAKE, and D and C red #7 CA LAKE. A series of tests were run to see if these dyes, and all such dyes, are soluable in the above bases. It was concluded that these dyes are soluable in all of the above described bases. A further test showed that these dyes are only slightly soluable in jojoba oil. However, the D and C dyes are very soluable in GMS. Since GMS is a common element in all of the above bases, it is understandable why the D and C dyes are soluable in all of the above bases. The dyes may be added to the molten GMS and mixed until a homogeneous solution is attained. The molten GMS and dye can then be easily dispersed into the jojoba oil for compositions with only a low concentration of GMS. The dye can also be added to molten solutions that have GMS and Jojoba oil, and mixed into the molten solutions. The fact that the D and C dyes are soluable in the above bases makes it possible to prepare lipsticks and rouges from them. The addition of 1 percent of pigments still produces a usable product that is almost exactly the same as the product without the pigment.

Some commercial lipsticks are more opaque and have better ability to hide the surface of the skin. One can improve the opacity of the above lipsticks by adding talc, magnesium carbonate, the iron oxide and other fillers. These fillers do not become absorbed into the above bases, but merely become suspended therein. The talc and magnesium carbonate have little effect on the physical attributes of the bases. However, the iron oxide pigments have a significant effect on the physical qualities of the bases.

While preferred embodiments of the invention have been shown and described, it will be apparent to those skilled in the art that changes can be made without departing from the principles and spirit of the invention, the scope of which is defined in the appended claims.

I claim:

1. A dermatological coating material prepared by combining 16 to 70 parts by weight of glyceryl monostearate with 84 to 30 parts by weight of a jojoba oil to form a solution with the aid of heat and mixing, which solution, when cooled, forms a frozen solution at room temperature.

2. A dermatological coating material as recited in claim 1, the preparation of the material including subjecting said frozen solution to a mixing under pressure step to reduce crystal formation.

3. A dermatological coating material as recited in claim 1, the preparation of the material including subjecting said frozen solution to an aging step at a slightly elevated temperature of substantially 95° F. for several days to reduce crystal formation.

4. A dermatological coating material as recited in claim 1, wherein said coating material is a lubricant, and wherein said glyceryl monostearate comprises 16 to 40 parts by weight and said jojoba oil component comprises 84 to 60 parts by weight.

5. A dermatological coating material as recited in claim 1 wherein said coating material is a stick cosmetic, and wherein said glyceryl monostearate comprises 40 to 70 parts by weight and said jojoba oil component comprises 60 to 30 parts by weight.

6. A dermatological coating material as recited in claim 1, wherein said coating material is a dermatological putty, and wherein said glyceryl monostearate comprises 60 to 70 parts by weight and said jojoba oil comprises 40 to 30 parts by weight.

7. A dermatological coating material as recited in claim 1, wherein said coating material is a hand lotion, and wherein said glyceryl monostearate comprises 30 parts by weight and said jojoba oil comprises 70 parts by weight.

8. A dermatological coating material as recited in claim 1, wherein said coating material resembles solid petrolatum.

9. A dermatological coating material as recited in claim 1, wherein said coating material is a cosmetic base.

10. A method of making a solution of glyceryl monostearate and jojoba oil comprising combining 16 to 70 parts by weight of glyceryl monostearate with 84 to 30 parts by weight of jojoba oil to form a solution with the aid of heat and mixing and permittng said solution to cool to form a frozen solution.

11. A method as recited in claim 10, further comprising the step of mixing said frozen solution under pressure to reduce crystal formation.

12. A method as recited in claim 10, further comprising the step of aging said frozen solution at a slightly elevated temperature of substantially 95° F. for several days to reduce crystal formation.

13. A method as recited in claim 12, wherein said slightly elevated temperature is 95° F. and said aging extends for a few days.

14. A method for hardening jojoba oil comprising combining at least 16 parts by weight of glyceryl monostearate with no more than 84 parts by weight of jojoba oil to form a solution with the aid of heat and mixing and permitting said solution to cool to form a frozen solution.

* * * * *